United States Patent [19]

Shah et al.

[11] Patent Number: 5,468,649

[45] Date of Patent: Nov. 21, 1995

[54] PROCESS FOR LABELING ACRIDINIUM TO MICROPARTICLES AND APPLICATION IN AN INSTRUMENT

[75] Inventors: Dinesh O. Shah, Vernon Hills; Tarun Chandra, Rolling Meadows; Kurt Klosterman, Gurnee, all of Ill.

[73] Assignee: Abbott Laboratories, Abbott Park, Ill.

[21] Appl. No.: 196,536

[22] Filed: Feb. 15, 1994

[51] Int. Cl.$^6$ .................. G01N 33/543; G01N 33/546
[52] U.S. Cl. .................. 436/518; 436/528; 436/531; 436/534; 422/52; 427/2.1; 427/2.11; 427/2.13
[58] Field of Search .................. 436/518, 528, 436/531, 533, 800, 805, 807; 427/2.1, 213.3, 213.31, 213.34, 213.36, 2.11, 2.13; 428/406, 402.24, 403, 407; 422/52; 435/7.72

[56] References Cited

U.S. PATENT DOCUMENTS

| 4,788,142 | 11/1988 | Hosako et al. | 435/29 |
| 5,089,424 | 2/1992 | Khalil et al. | 436/518 |

OTHER PUBLICATIONS

Okubo et al Colloid Polym. Sci. 268 pp. 598–603 (1990) "Preferential Adsorption of Bovine Serum Albumin Diner onto Polymeric Microspheres having a Heterogenous Surface Consisting of Hydrophobic and Hydrophilic Parts".
Hart et al. J. Imm. Meth. 101 pp. 91–96 (1987) "The Use of Arridinium Ester–Labelled Strepavidin in Immunoassays".
"A chemiluminescent, microparticle–membrane capture immunoassay for the detection of antibody to hepatitis B core antigen", Journal of Immunological Methods, 133 (1990) 191–198.
Particle Technology News, ImmunoPure® Immobilized D–Biotin Spring 1992, vol. 3, No. 1, pp. 1–3.
Journal of Immunological Methods, P. Vincent, et al. "A comparison of the binding of biotin and biotinylated macromolecular ligands to an anti–biotin monoclonal antibody and to streptavidin", 165 (1993), pp. 177–182.
Journal of Bioluminescence and Chemiluminescence, P. E. Stanley, "A Survey of more than 90 Commercially Available Luminometers and Imaging Devices for Low–light Measurements of Chemiluminescence, Including Instruments for Manual, Automatic and Specialized Operation, for HPLC, LC, GLC and Microtitre Plates" vol. 7 (1992), pp. 77–108.
Immuno Technology Catalog and Handbook, 1991, "Introduction to Avidin–Biotin Systems in Immunochemistry".

Primary Examiner—Toni R. Scheiner
Assistant Examiner—Lora M. Green

[57] ABSTRACT

Embodiments of the invention provide methods of preparing an activated acridinium microparticle. Generally, the methods involve direct covalent coupling or an affinity format. The direct covalent coupling method involves coating a microparticle with a proteinaceous compound. Then, a 10-methyl-N-tosyl-N-(2-carboxyethyl)-9-acridinium carboximide trifluoromethane sulfonate is coupled to the proteinaceous compound. In the affinity format, a microparticle is coated with a biotinylated proteinaceous compound. The microparticle is reacted with an anti-biotin labelled 10-methyl-N-tosyl-N-(2-carboxyethyl)-9-acridinium carboximide trifluoromethane sulfonate. Methods are also provided for using such a microparticle. Those methods of use can estimate transfer efficiency, calibrate optics, and measure membrane pore size of a chemiluminescence based instrument. Test elements for analytical instruments are also provided.

12 Claims, 11 Drawing Sheets

TRANSFER EFFICIENCY COMPARISON BETWEEN AFFINITY FORMAT LABELED AND ANTI-HBsAg LABELED ACTIVATED MICROPARTICLES

|  | TRANSFER EFFICIENCY_A | TRANSFER EFFICIENCY_B |
|---|---|---|
| AFFINITY FORMAT MICROPARTICLES | 101.50% | 102.50% |
| ANTI-HBsAg MICROPARTICLES | 101.00% | 102.30% |

PROCESS FOR LABELING ACRIDINIUM TO MICROPARTICLES AND APPLICATION IN AN INSTRUMENT

BACKGROUND OF THE INVENTION

The present invention relates to methods and compounds for use with an instrument for performing chemical assays and measurements and, more particularly, to methods and compounds for chemiluminescence-based tests on an instrument employed in performing chemical assays, such as those performing quantitative and qualitative tests on chemical and biochemical solutions.

A variety of assay methods and compounds are employed in quantitative and qualitative analyses of chemical and biochemical mixtures. In some instances, those quantitative and qualitative analyses are performed by an instrument. Certain of the methods and compounds employed in analyses can be useful in testing the instrument employed in those analyses. Such tests may concern, for example, transfer efficiencies, instrument calibrations, membrane pore size measurements, and the like. A number of methods and compounds employed in these tests regarding instruments are known. New methods and compounds and improvements in existing methods and compounds, however, are being developed.

One chemical property utilized in certain analytical applications, including tests regarding instruments is referred to as "chemiluminescence". Chemiluminescence is the emission of light as the result of a chemical reaction. Chemiluminescence occurs when products of a chemical reaction are excited and emit light.

In an exemplary chemical reaction that generates chemiluminescence, a step of the reaction is a chemiexcitation step (which may be unimolecular or bimolecular) which achieves conversion of chemical energy into electronic excitation energy. In the reaction, a product molecule receives chemical energy and converts it to an excited electronic state. This electronically excited product molecule then produces light or luminesces under reaction conditions.

Attempts have been made to automate chemiluminescence measurements. Some attempts have involved a variety of instruments, such as, for example, the use of photographic film and a densitometer to record a chemiluminescent signal from a reaction in clear microtitration plates.

To provide accurate and desired results, measurements and other determinations regarding the systems may be made periodically. These determinations may indicate the condition of the system involved.

For instance, chemiluminescence may be useful in measuring transfer efficiencies and/or other aspects of instruments employed to perform assays which are measured or observed by chemiluminescent characteristics. Instruments which are capable of conforming to minute tolerances in these regards have relatively high transfer efficiencies. Instruments that do not yield accurate component measurements on transfer have relatively low transfer efficiencies. To perform accurate tests with some analytical instruments, knowledge of transfer efficiencies (and, thus, the inherent accuracies and inaccuracies of the instruments) is desirable.

It is known to make certain tests on instruments used to perform assays and other tests for determining the accuracy and the like of the instrument. A known method for making such tests performs particular assays on a standard sample of known composition and characteristics. Because the composition and characteristics of the standard sample are known, results of assays and tests performed with the sample should yield expected results if the instrument were to perform accurately. If expected results were not obtained, inaccuracies of the instrument being utilized may be indicated.

It is known to perform particular tests on the instrument used. In so testing instruments, acridinium activated particles may be used as a standard sample. Acridinium, when reacted with alkaline peroxides, yields a light producing reaction. Some currently available acridinium activated particles used in testing chemiluminescence-based instruments have certain disadvantages. One such disadvantage involves the method of preparing these particles. In this prior method, latex particles are coated with anti-HBsAg labelled acridinium using passive adsorption. Then, activated acridinium is passively adsorbed onto the particle surfaces.

The product activated acridinium microparticles obtained from some prior methods may be disadvantageous for use in testing some chemiluminescence-based instruments. The light emission profiles of particles may not be sufficiently identical to or closely resemble the actual light emission profiles of chemiluminescence-based immunoassays. It is desirable that a standard sample for testing perform substantially the same as an unknown will perform when tested. However, this may not always be the case. A possible reason for differences in light emission of some currently available product activated acridinium microparticles may be stearic hindrance effects caused by acridinium loading.

SUMMARY OF THE INVENTION

The embodiments of the present invention provide a number of methods for manufacturing an activated acridinium microparticle as well as methods of using such a microparticle with an instrument. According to one embodiment, a method of preparing an activated acridinium microparticle includes coating a microparticle with a proteinaceous compound and coupling a 10-methyl-N-tosyl-N-(2-carboxyethyl)-9-acridinium carboximide trifluoromethane sulfonate to the proteinaceous compound.

According to another embodiment of the invention, another method of preparing an activated acridinium microparticle comprises coating a microparticle with a biotinylated proteinaceous compound. Then, the microparticle is reacted with an anti-biotin labelled 10-methyl-N-tosyl-N-(2-carboxyethyl)-9-acridinium carboximide trifluoromethane sulfonate.

According to an additional embodiment of the invention, a method of testing an analytical instrument is provided. A microparticle is coated with a proteinaceous compound. A 10-methyl-N-tosyl-N-(2-carboxyethyl)-9-acridinium carboximide trifluoromethane sulfonate is coupled to the proteinaceous compound. The 10-methyl-N-tosyl-N-(2-carboxyethyl)-9-acridinium carboximide trifluoromethane sulfonate is activated to obtain an activated acridinium microparticle. Alternatively, the microparticle is prepared by coating it with a biotinylated proteinaceous compound. The microparticle is reacted with an anti-biotin labelled 10-methyl-N-tosyl-N-(2-carboxyethyl)-9-acridinium carboximide trifluoromethane sulfonate. The thusly produced microparticle may be used in a test on the instrument. The test may determine or estimate transfer efficiency, calibrate instrument optics, measure membrane pore size or other tests. The instrument may be a chemiluminescence based instrument.

Yet further embodiments of the invention provide test elements for use in an analytical instrument. The test element comprises a microparticle coated with a proteinaceous compound. Then a 10-methyl-N-tosyl-N-(2-carboxyethyl)-9-acridinium carboximide trifluoromethane sulfonate is coupled to the proteinaceous compound on the microparticle. Alternatively, a microparticle is coated with a biotinylated proteinaceous compound. Then, an anti-biotin labelled 10-methyl-N-tosyl-N-(2 -carboxyethyl)-9-acridinium carboximide trifluoromethane sulfonate is reacted with the microparticle.

DETAILED DESCRIPTION OF PREFERRED EMBODIMENTS

Disclosed in the following paragraphs are methods of preparation of compounds and compounds for chemiluminescence-based determinations about automated instrumentation and equipment employed in performing immunoassays. Microparticles made according to these methods may be used with a variety of suitable instruments to perform desired tests.

Two methods for preparing activated acridinium microparticles representing embodiments of the present invention are disclosed. One is referred to herein as "direct covalent coupling". In direct covalent coupling, activated methyl acridinium is directly coupled by covalent bonding to bovine serum albumin ("BSA") coated microparticles. The second method is referred to herein as "affinity format". In affinity format, anti-biotin labelled methyl acridinium is reacted in order to conjugate with biotinylated BSA coated microparticles. Certain specific procedures for these two methods are hereinafter described. In an exemplary embodiment, the microparticles may be made of a suitable polymer, such as latex, polystyrene and the like. It is to be remembered that variations of these methods are also possible. The steps disclosed herein may be performed in any suitable order, and steps of one method may be combined with steps of another method.

Figure 1:
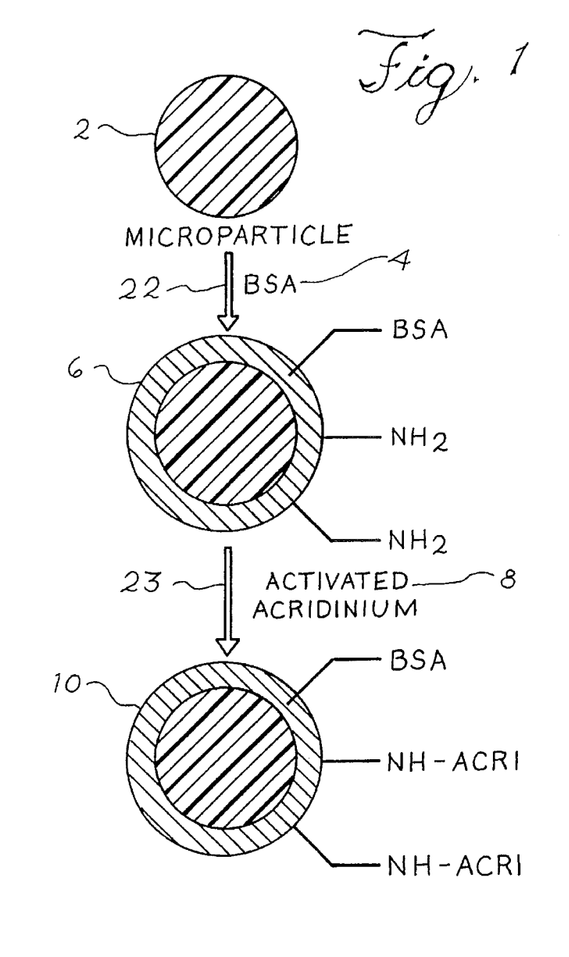
FIG. 1 is a flow chart of a method of preparing activated acridinium microparticles by direct covalent coupling.

Referring now to FIG. 1, a flow diagram of the direct covalent coupling method for preparing activated acridinium microparticles is illustrated. Generally, the direct covalent coupling method in this embodiment comprises three steps. A first step (not shown in detail) is an activation step in which 10-Methyl-N-tosyl-N-(2-carboxyethyl)-9-acridinium carboximide trifluoromethane sulfonate (abbreviated as "methyl acridinium" herein) 8 is activated. In a second step, a coating step 22, microparticles 2 are coated with BSA 4. Finally, in a third step, which is a coupling step 23, amino groups of the BSA coated on the surface of the microparticles 6 is covalently coupled to the activated methyl acridinium 8.

The first (or activation) step is initiated by adding approximately 510 µl of N-Hydroxy succinimide solution (about 10 mg/1.74 ml dimethylformamide) and about 510 µl of 1-ethyl-3 (dimethylaminopropyl) carbodiimide ("EDA-C")(about 10 mg/1.31 ml dimethylformamide) to a solution containing about 10 mg of methyl acridinium in about 1.04 ml of dimethylformamide ("DMF"). This mixture is stirred at ambient temperature in the absence of light for a period of about 12 to about 16 hours. The activation is monitored using thin layer chromatography. When the activated product 6 is obtained, the product is used for coupling to protein without purification.

Continuing to refer to FIG. 1, the coating step 22 begins with centrifugation of particles 2, such as polystyrene particles (for example, 2.5 µm, Spherotech, 1 ml, 5% w/v) and the like. The particles 2 are centrifuged at about 11,000×g for approximately 5 minutes and the supernatant is decanted. After centrifugation, the packed particles 2 are resuspended in about 1 ml of phosphate buffered saline ("PBS"), which is about 0.01M sodium phosphate, about 0.15M sodium chloride, a pH of about 7.2, and the centrifugation step is repeated. Other buffers may be used. The packed particles 2 from this second centrifugation step are then resuspended in about 1 ml of BSA solution 4 (about 2 mg/ml in PBS) and the mixture is tumbled at ambient temperature for period of about 16 hours. The suspension obtained from the tumbling is then centrifuged at about 11,000×g for about 5 minutes and the supernatant is decanted. Particles obtained from this tumbling are then washed, preferably three times, each with about 1 ml of PBS by centrifugation and resuspension. The BSA coated particles 6 obtained are then resuspended in about 5 ml of PBS to give an approximate 1% w/v suspension.

Further still referring to FIG. 1, in the coupling step 23, the BSA coated particles 6 (for example 0.5 ml, 1% w/v in an exemplary embodiment) obtained from the coating step 22 are added to about 72 μl of conjugate buffer (about 0.1M PBS, with approximately 0.1% CHAPS, pH of about 6.3) and about 15 μl of the activated methyl acridinium 8 (about 5 mg/1 ml DMF) obtained from the activation step. The mixture is then gently tumbled for about 30 minutes at ambient temperature. The particles obtained 10 are then centrifuged at about 11,000×g for about 5 minutes, washed by centrifugation, preferably three times, and then resuspended as before in the second (or coating) step. The particles are resuspended in about 1 ml of PBS to give an approximate 0.5% w/v particles 10.

Figure 2:
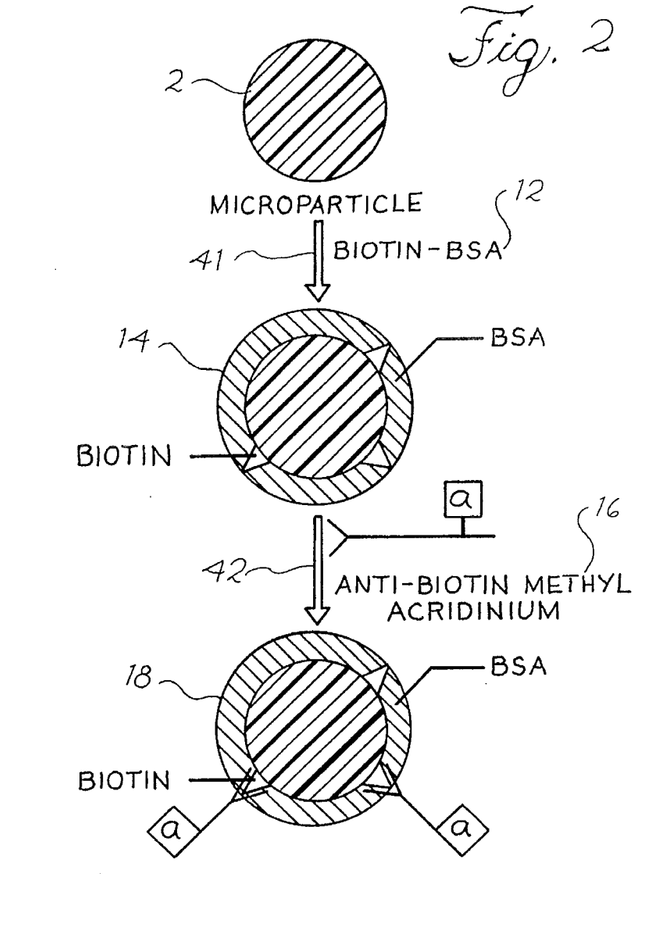
FIG. 2 is a flow chart of a method of preparing activated acridinium microparticles by affinity format.

Now referring to FIG. 2, a flow diagram of the affinity format method for preparing activated acridinium microparticles is illustrated. Generally, the affinity format method includes two steps. The first of the steps, a coating step 41, involves the coating of biotinylated BSA 12 to microparticles 2. The second step, an affinity reaction step 42, includes an affinity reaction wherein anti-biotin labelled methyl acridinium 16 is conjugated to biotinylated BSA coated microparticles 14.

Continuing to refer to FIG. 2, details of each of the two steps of the affinity format method may be described in detail. In the first, or coating, step 41 microparticles 2, preferably polystyrene particles (for example, about 2.5 μm, Spherotech, approximately 1 ml of 5% w/v), are centrifuged at about 11,000×g for about 5 minutes and the supernatant is decanted. The packed particles 2 from that centrifugation are then resuspended in about 1.5 ml of biotinylated BSA solution 12 (for example, Sigma, about 1 mg/ml in PBS, pH of approximately 7.2) and the mixture is tumbled at ambient temperature for about 20 hours. The suspension obtained from the tumbling is then centrifuged at about 11,000×g for about 5 minutes and the supernatant is decanted. Particles obtained from this tumbling are then washed, preferably three times, each with about 1 ml of PBS by centrifugation and resuspension. The BSA coated particles 14 obtained are then resuspended in about 5 ml of PBS to give an approximate 1% w/v suspension.

Further still referring to FIG. 2, in the affinity reaction step 42 of the affinity reaction method, the biotinylated BSA coated particles 14 (about 1 ml of about 1% w/v) of the coating step 41 of the affinity reaction method are centrifuged at about 11,000×g for approximately 5 minutes and the supernatant is decanted. The packed particles 14 obtained from the centrifugation are then resuspended in about 1 ml of anti-biotin labelled with methyl acridinium 16. This amount of anti-biotin labelled with methyl acridinium 16 is obtained from a solution of about 40μl of anti-biotin acridinium (approximately 250 μg/ml, protein concentration, Acridinium/IgG is about 1.8) added to approximately 9,960 ml of conjugate diluent, said conjugate diluent being comprised of about 40% calf serum, about 10% normal human plasma, about 100 mM phosphate buffer, with a pH of about 6.3, and about 0.15M NaCl in an exemplary embodiment. The mixture of packed particles resuspended in the anti-biotin labelled with methyl acridinium 16 is then tumbled for about 16 hours at ambient temperature in the absence of light. The particles 18 obtained from the tumbling are centrifuged at about 11,000×g for about 5 minutes, washed, preferably three times, by centrifugation, and then resuspended as before in this affinity reaction step. The activated acridinium microparticles 18 are resuspended in about 10 ml of PBS to give approximately 0.1% w/v particles.

Now referring to FIGS. 1 and 2 in conjunction, procedures similar to those described in detail above for preparing activated acridinium microparticles according to the direct covalent coupling method and the affinity format method may be employed to prepare activated microparticles 10, 18 of various sizes, such as, for example, about 3.5 μm, 4.5 μm, 5 μm and 6 μm. In addition, though specific procedures have been described herein with respect to each of the direct covalent coupling method and the affinity format method, those procedures are intended only for clarifying understanding. Though the exemplary embodiments are described in detail, it is intended and should be understood that those skilled in the art will understand that various changes, additions, modifications, and alternatives are possible in the specific procedures in keeping with the embodiments described herein.

Figure 3A:
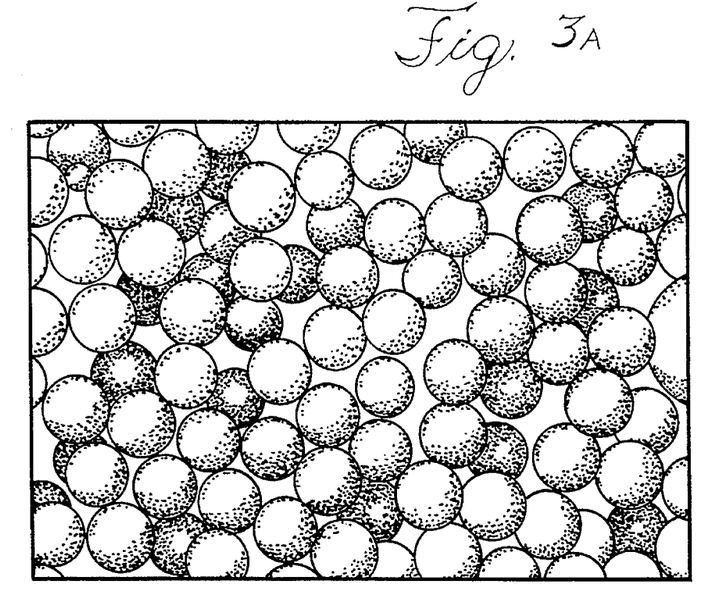
FIGS. 3A–C are scanning electron micrograph depictions of 2.3 µm and 4.0 µm affinity format labelled activated acridinium microparticles, respectively.
Figure 3B:
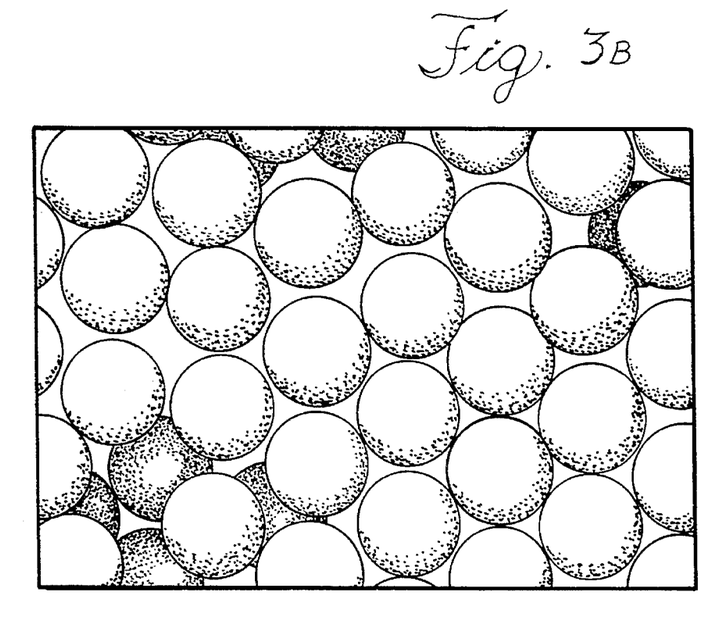
Figure 3C:
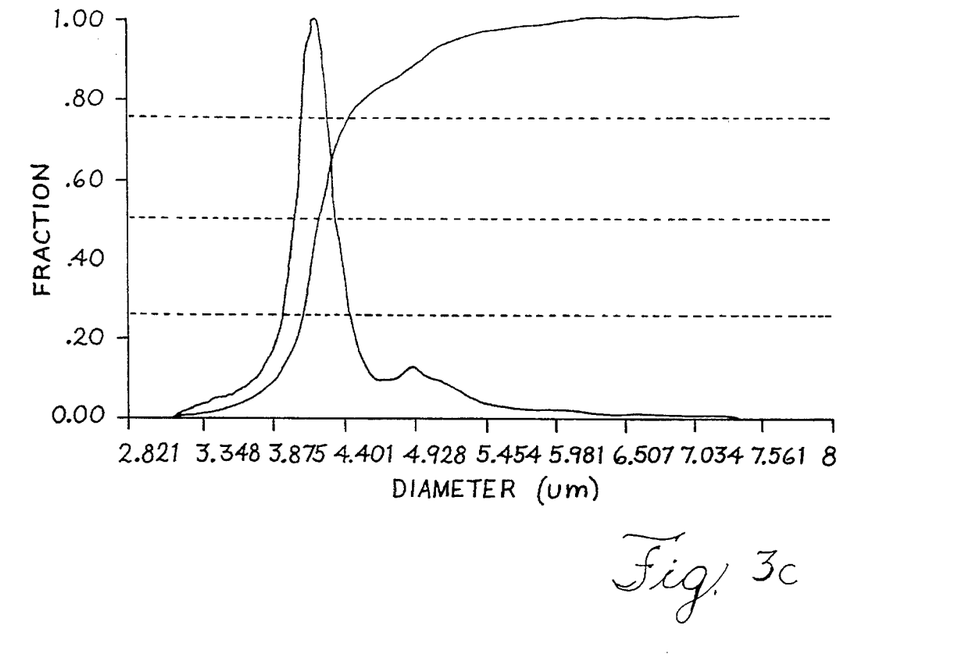
Figure 4A:
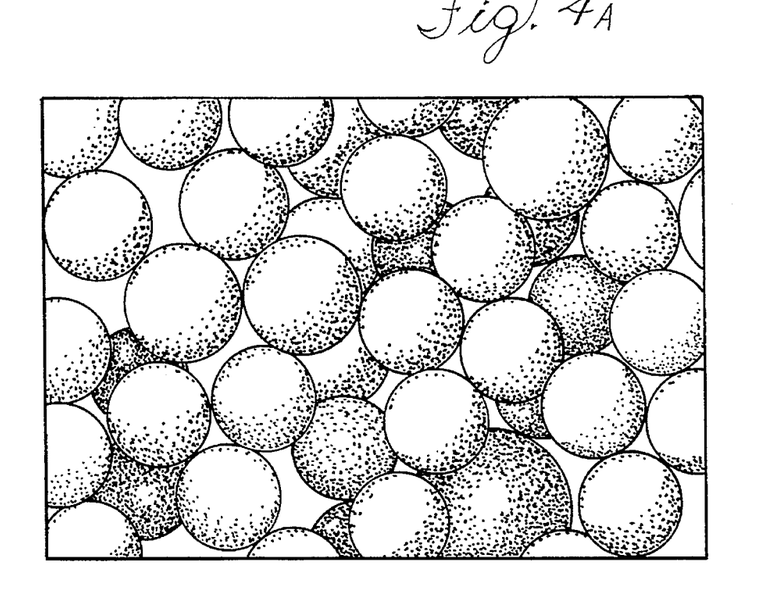
FIGS. 4A–C are scanning electron micrograph depictions of 3.5 µm and 6.0 µm affinity format labelled activated acridinium microparticles, respectively.
Figure 4B:
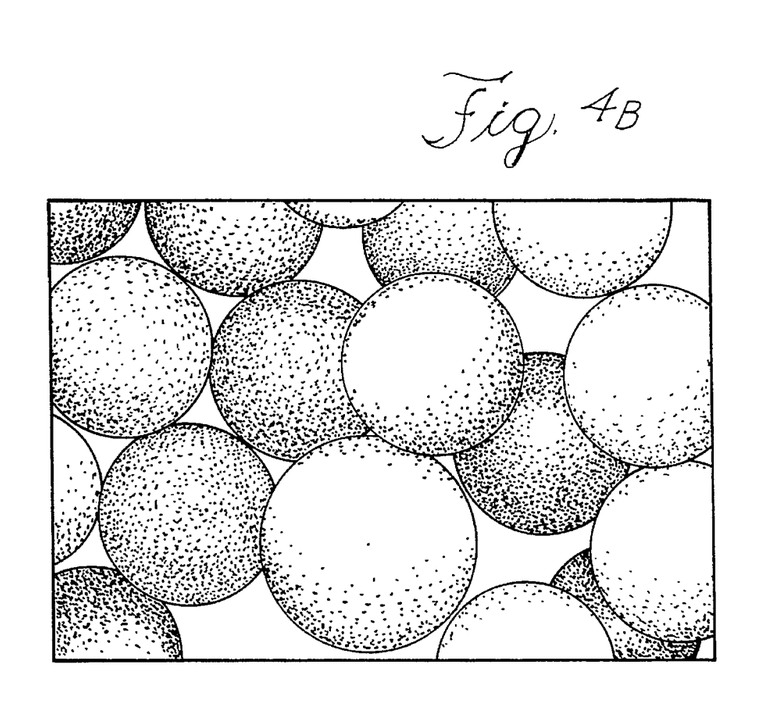
Figure 4C:
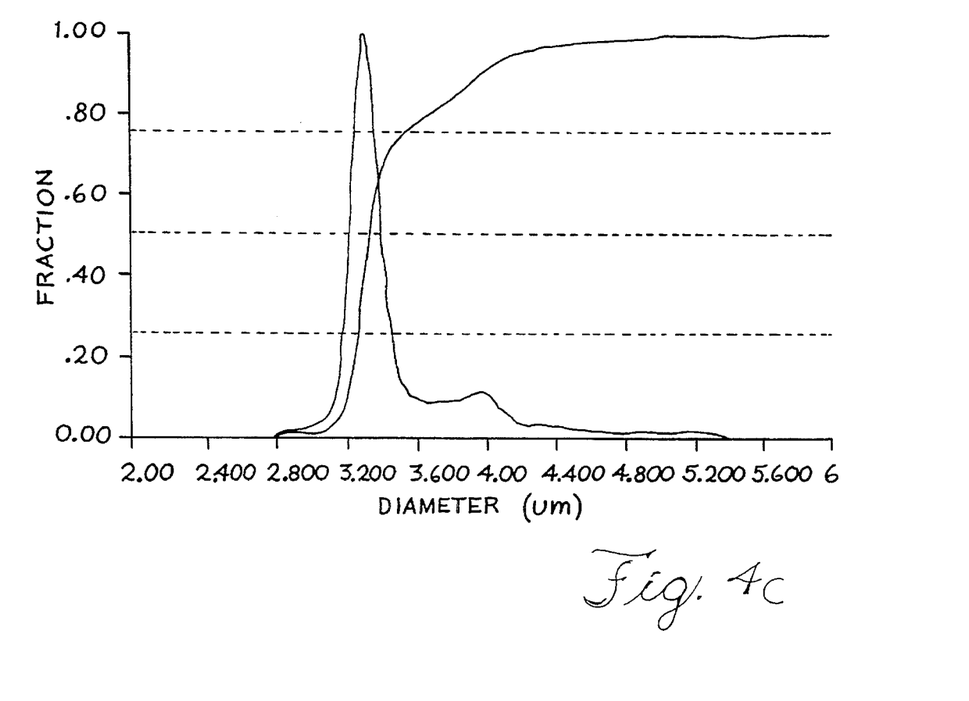

Next referring to FIGS. 3A–C and 4A–C, certain scanning electron micrographs of 2.3 μm, 4.0 μm, and 3.5 μm and 6.0 μm activated acridinium microparticles and graphs tracking the size distribution of 4.0 μm and 3.5 μm are shown. The activated acridinium microparticles shown in the micrographs were prepared in accordance with the affinity format method. The micrographs shown in FIGS. 3A–B and 4A–B are provided, in particular, to show the high monodispersity and uniform size of the 2.3 μm, 4.0 μm, 3.5μ and 6.0 μm microparticles 18, respectively, obtained from the affinity format method. FIGS. 3C and 4C show, in particular, the size distribution of 4.0 μm and 3.5 μm activated acridinium microparticles 18, respectively.

Figure 5:
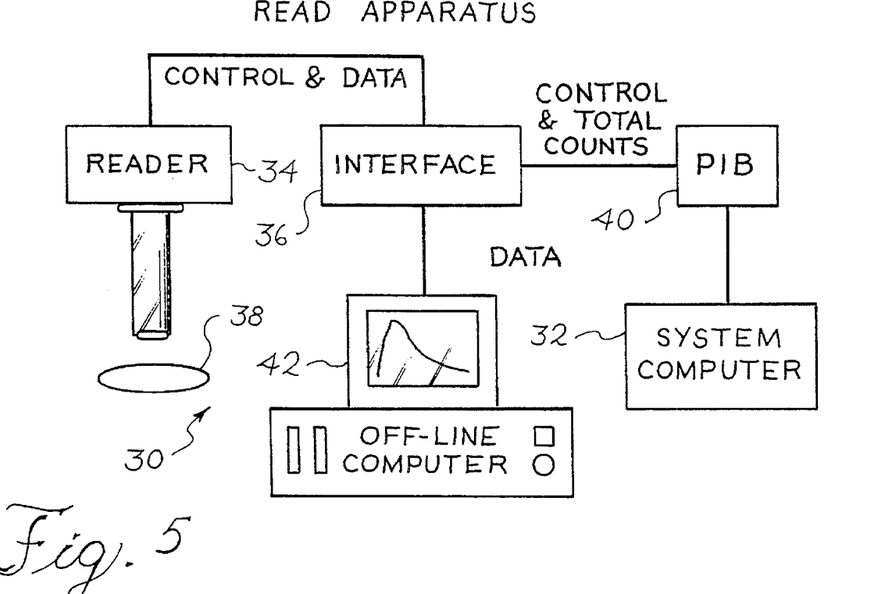
FIG. 5 is a simplified, block diagram illustration of a millisecond read system, including a microcomputer based automated data acquisition system, for detecting photon count information.

Now referring to FIG. 5, a read system 30 for measuring performance of activated acridinium microparticles 18 prepared according to the affinity format method is illustrated. The read system 30 employs a millisecond read technique. The read system 30 comprises a microcomputer 32 based automated data acquisition system. The system is equipped with an electronic interface board 40 capable of acquiring photon count information, generated by optics, such as a reader 34. An interface 36 may also be used to synchronize the start of a data acquisition cycle, for example, with the dispensing of activator solution at the read station 38. The read system 30 accumulates a running sum of photon counts acquired during a read cycle of approximately 2 seconds with temporal acquisitions taken and recorded at about 10 ms intervals. Accumulated data can be used, for example, to obtain incremental counts for every read interval, thus, yielding light emission profiles, generated, for example, at an off-line computer terminal 42, substantially similar to those obtained in a chemiluminescence reaction. FIGS. 6, 7A, 7B, 8 and 9 may be obtained by subtracting subsequent approximately 10 ms intervals to arrive at the number of events per about 10 ms interval, for example. The about 10 ms events are plotted over time to produce a rate reaction profile.

Still referring to FIG. 5, a procedure for assessing performance of activated acridinium microparticles 10,18, for example, those prepared according to the affinity format method may be understood. This procedure is substantially similar to that which may be performed on an analytical instrument. The procedure may be initiated by pipetting about 50 μl of activated acridinium microparticle directly on a reaction matrix in one or more reaction vessels. The particles may then be washed by pipetting about 100 μl of wash solution directly on the matrix. The reaction vessels may then be transferred to a read station. Then, employing the read system 30, chemiluminescence photon counts may be obtained. About 85 μl of an activator solution is dispensed onto the reaction tray matrix thus triggering the chemiluminescence reaction. Next, net photon counts and incremental photon counts are each obtained from the read system 30. The net photon counts are the difference between the total activated counts and the previously recorded dark counts taken over, for example, about a 2 second read time. The net photon counts and incremental photon counts serve for comparison to chemiluminescence reactions observed by the read system 30 in order to assess performance of the activated acridinium particles 18.

Figure 6:
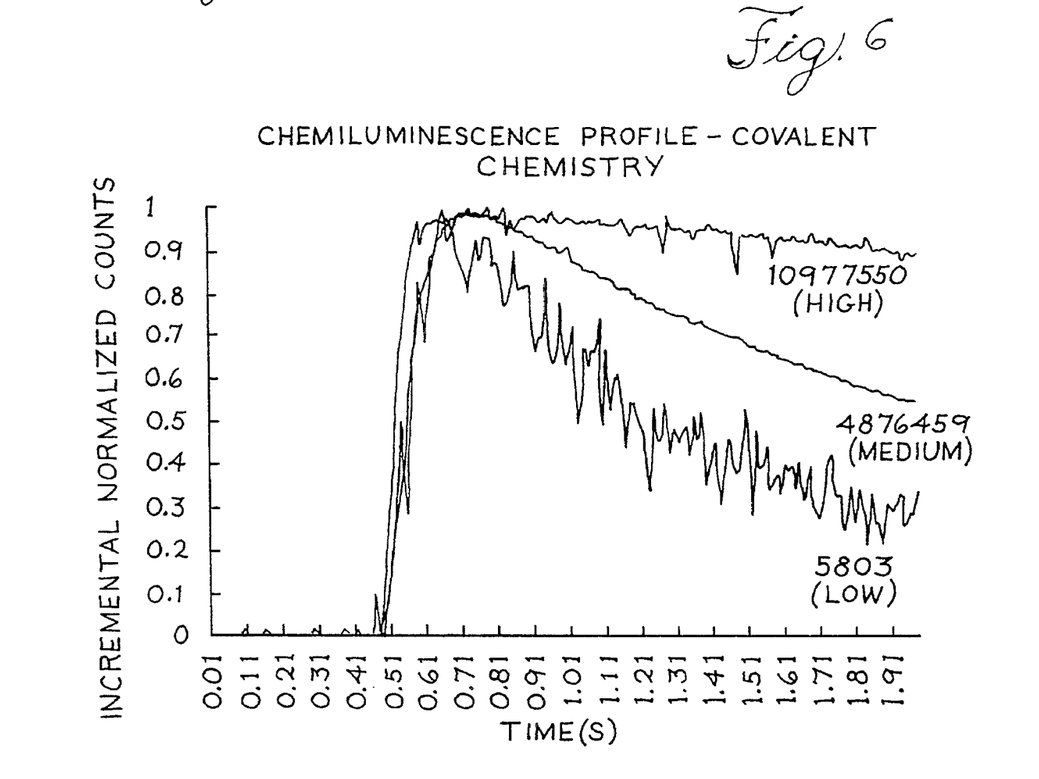
FIG. 6 is a chemiluminescence light emission profile illustrating decay rate at varying concentrations of anti-biotin acridinium conjugate loading on covalently coupled (about 0.002%) 2.5 µm biotinylated latex particles.

Next referring to FIG. 6, certain chemiluminescence light emission profiles are shown. These light emission profiles have been determined for activated acridinium microparticles prepared according to the direct covalent coupling method. The profiles in FIG. 6 illustrate varying concentrations of anti-biotin acridinium conjugate loading on the covalently coupled (about 0.002%) 2.5 μm biotinylated microparticles. Note that the profiles vary depending upon loading, in particular, with respect to the decay rate of the chemiluminescence light emission profile. Stearic hindrance effects caused by acridinium loading may cause light emission profiles of activated acridinium microparticles to be dissimilar to profiles of chemiluminescence reactions.

Figure 7A:
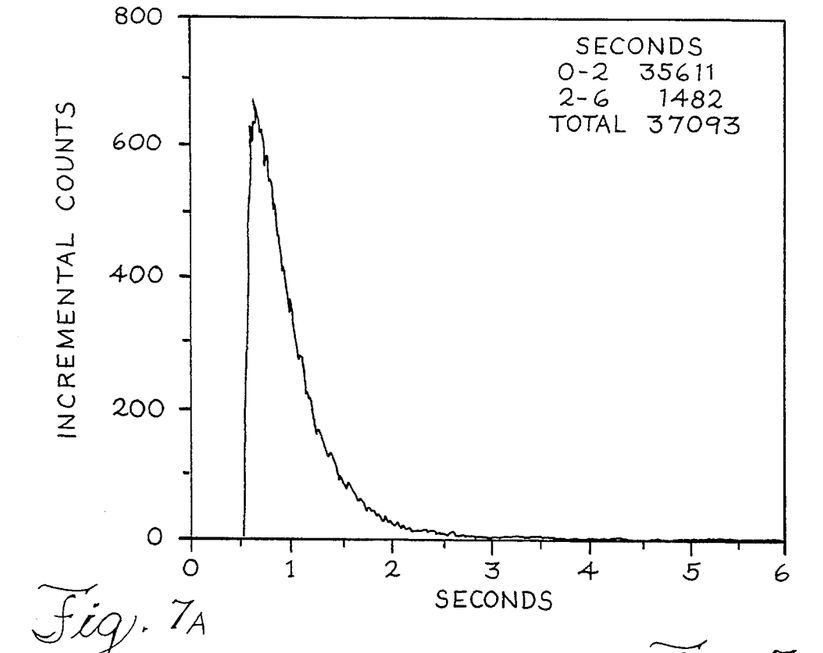
FIG. 7A is a light emission profile for a HBsAg assay.
Figure 7B:
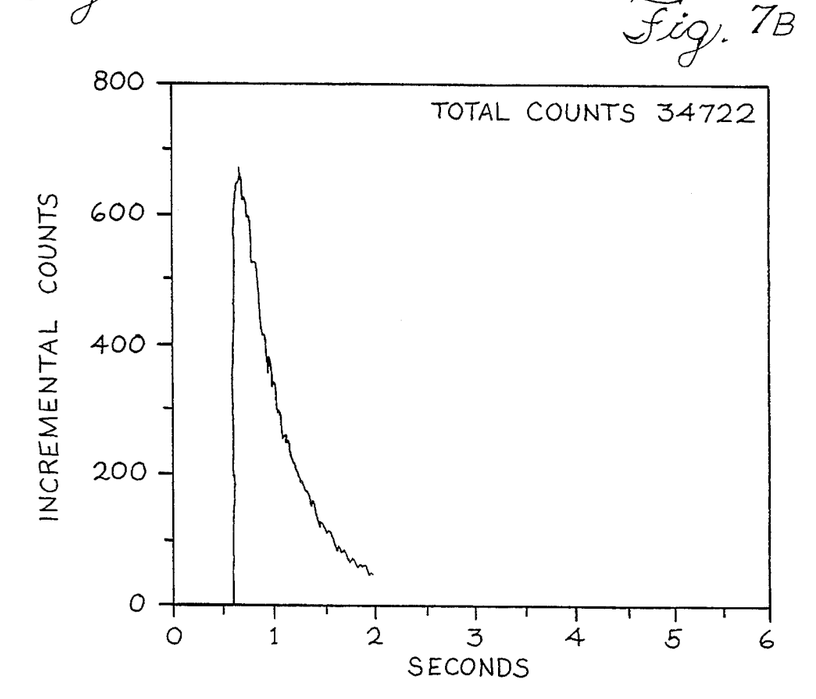
FIG. 7B is a light emission profile for a 2.5 µm affinity format labelled activated acridinium microparticle.

Now referring to FIG. 7A, a chemiluminescence light emission profile for an HBsAg assay positive sample is shown. Continuing to refer to FIGS. 7A and 7B, light emission profiles for the chemiluminescence-based HBsAg assay and a 2.5 μm affinity format labelled activated acridinium microparticle may be compared. Note the similarity of the two profiles.

Figure 7C:
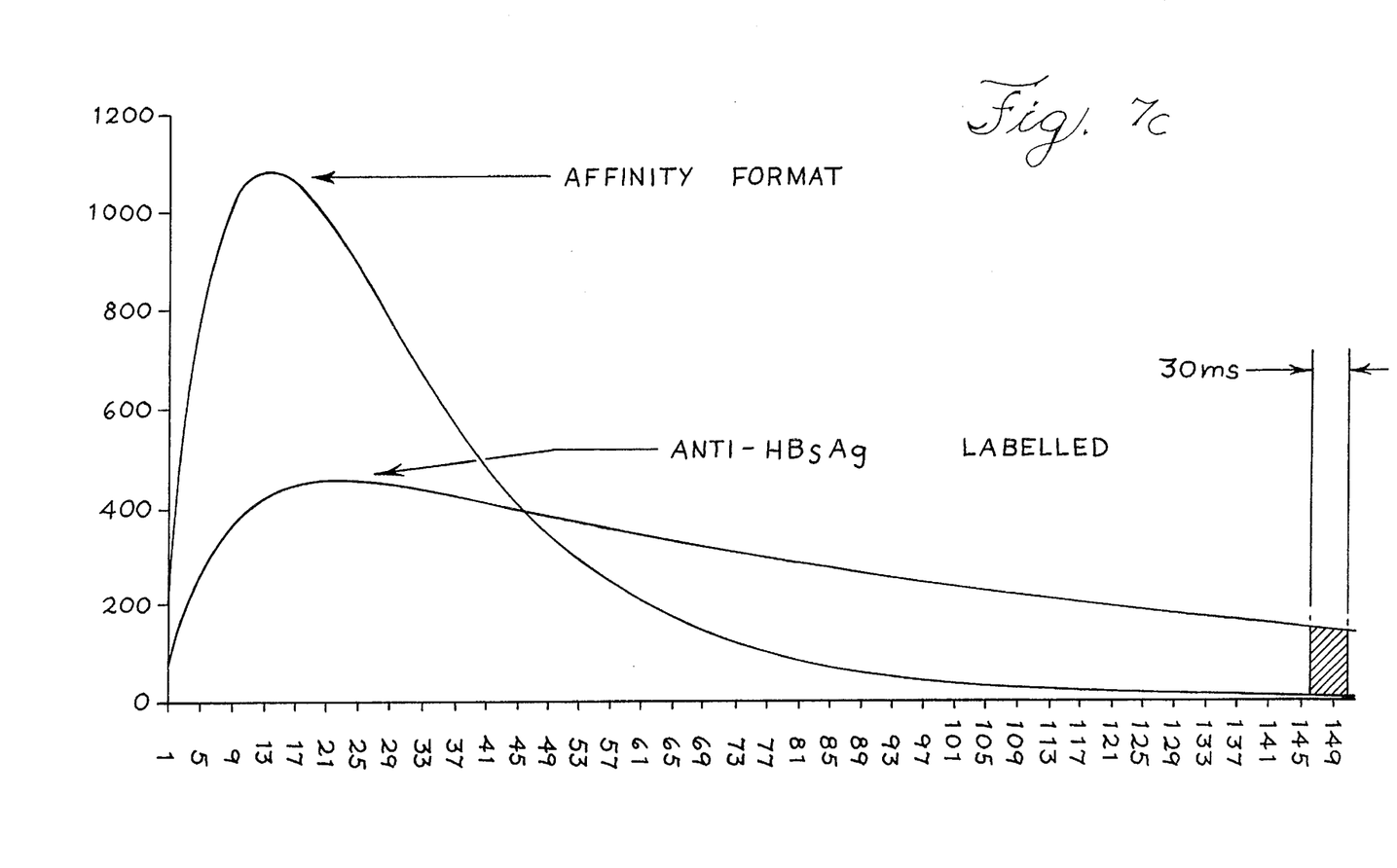
FIG. 7C is a comparison of light emission profiles for an affinity format labelled activated acridinium microparticle and for an anti-HBsAg labelled microparticle.

Drawing attention to FIG. 7C, the chemiluminescence profiles for an affinity format labelled acridinium microparticle are shown having a decay time of approximately 1.52 seconds. Since the tail of the chemiluminescence profile resembles an exponential decay, the last about 20 to 30 ms of the approximately 1.52 second decay time contains less than about 0.02% of the total chemiluminescence counts. In comparison, the similar profiles for the anti-HBsAg coated microparticles have decay times substantially larger than about 2 seconds. As much as about 1% of the total chemiluminescence counts may be contained in the last about 20 to 30 ms of the same approximately 1.52 second decay time, i.e. the profile has not decayed completely. For optics calibration, for instance, a number, such as four, increasing levels of acridinium activated microparticles may be used and a slope may be obtained for each reader using chemiluminescence counts. If an about 1% error in timing the actual chemiluminescence profile were assumed, then error in estimating the slope for a given reader may be as large as 1.2% for the anti-HBsAg coated microparticle. It is notable that, under similar conditions, the error in estimating reader slope for an affinity format labelled microparticle is only about 0.023%.

Figure 8:
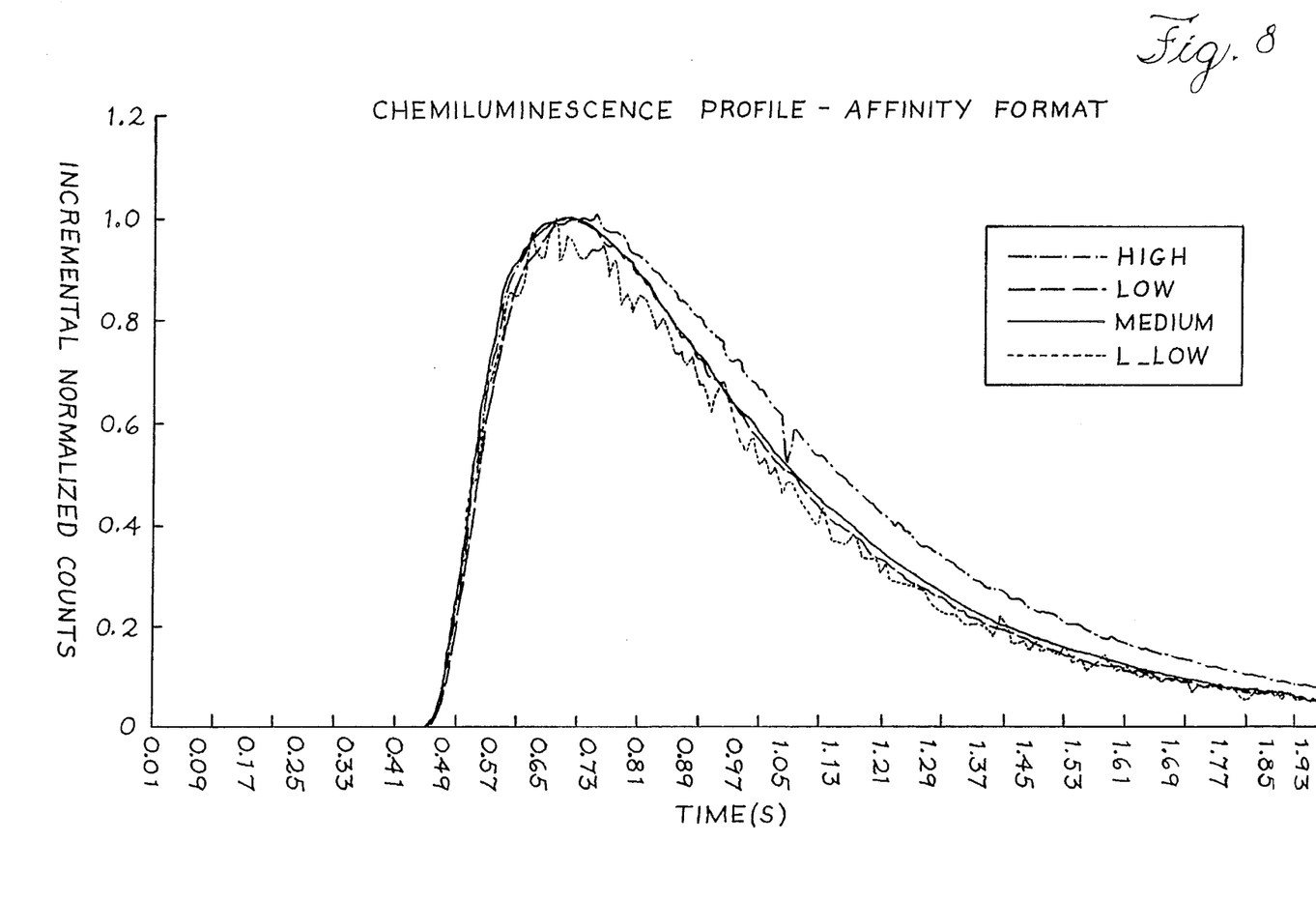
FIG. 8 is a chemiluminescence light emission profile illustrating the effect of varying concentrations of acridinium loading on (about 0.001%) 2.5 µm affinity format labelled particles.

Next referring to FIG. 8, additional chemiluminescence light emission profiles are shown. These profiles show the effect of varying concentrations of acridinium loading when activated acridinium microparticles are prepared in accordance with the affinity format method. These particular profiles are for (about 0.001%) 2.5 μm affinity format labelled particles. Note that acridinium loading does not significantly affect the chemiluminescence light emission profiles of activated acridinium microparticles. At each loading level (i.e., high, medium, low, and l_low), the light emission profile is approximately the same. For this reason, improved results and significant advantages are provided by particles prepared according to the embodiments of the methods described in detail herein.

Figure 9:
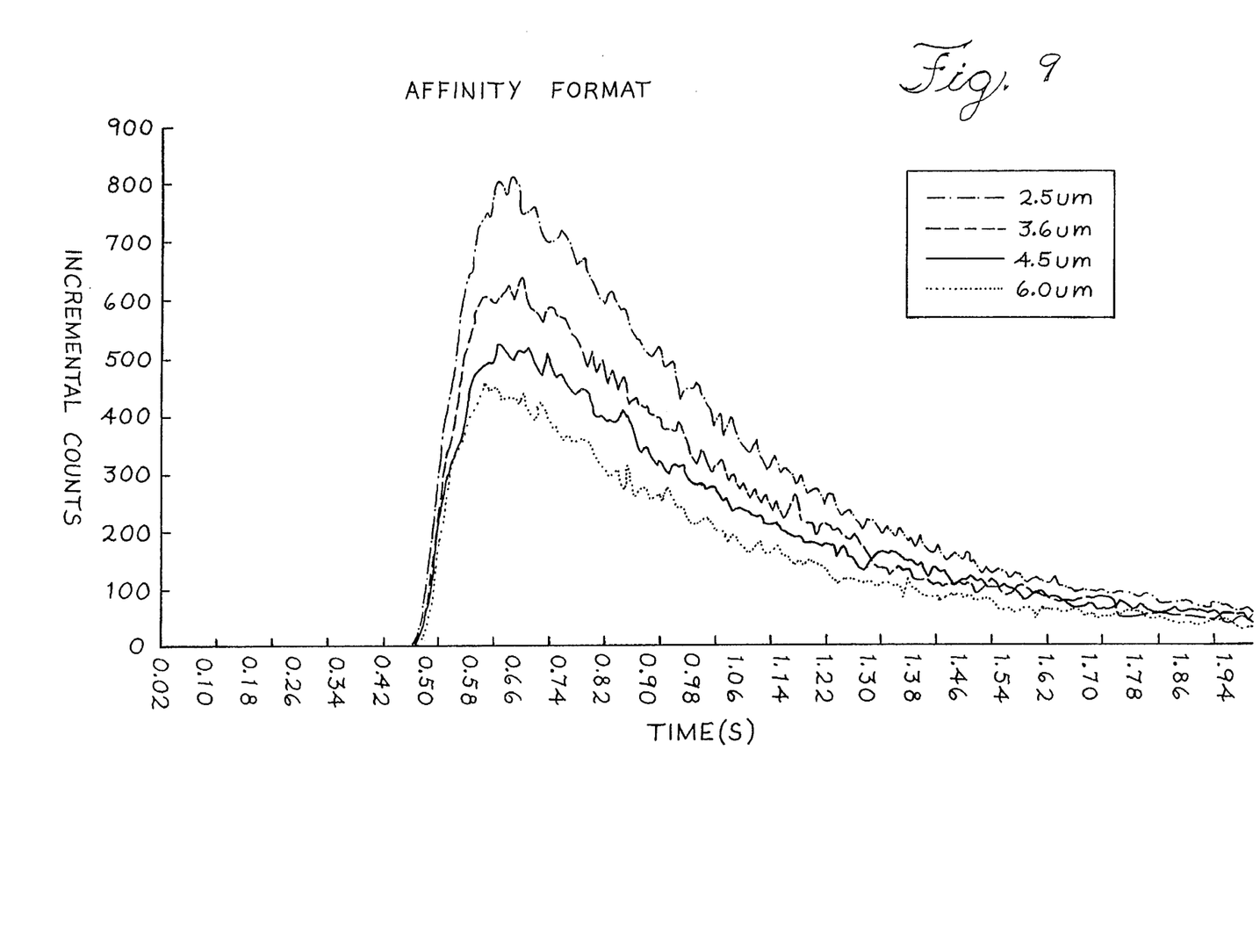
FIG. 9 is a chemiluminescence light emission profile of (about 0.002%) 2.5 µm, 3.6 µm, 4.5 µm and 6.0 µm affinity format labelled particles.

Now referring to FIG. 9, additional chemiluminescence light emission profiles are shown. Each of these profiles is for activated acridinium microparticles prepared according to the affinity format method. The profiles differ only because different microparticle sizes are employed in the chemiluminescence light emission measurements. Even given that the microparticle sizes vary, note the similarities in the chemiluminescence profiles for each of the (about 0.002%) 2.5 μm, 3.6 μm, 4.5 μm and 6.0 μm affinity format activated acridinium microparticles, respectively. These particular characteristics of the activated acridinium microparticles offer significant advantages in the technology.

Figure 10:
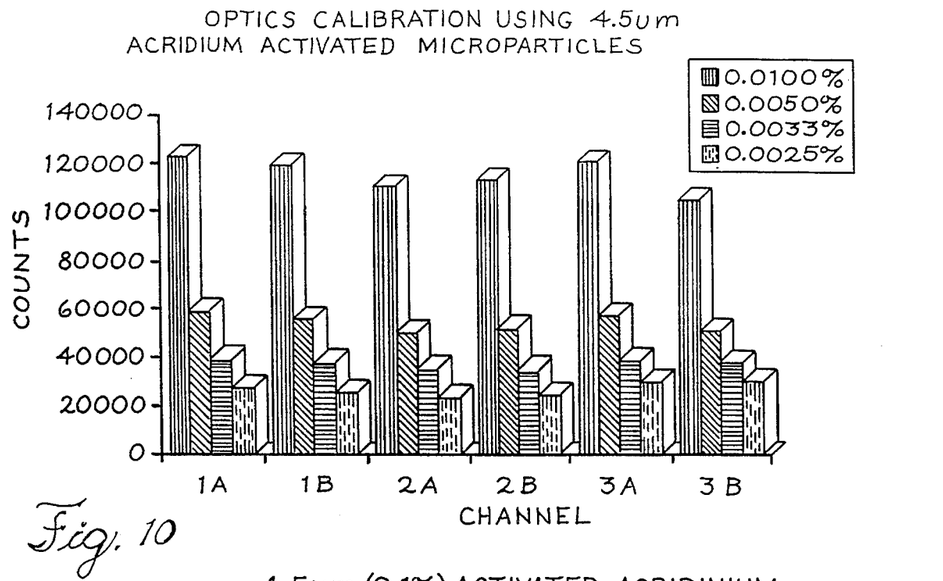
FIG. 10 illustrates the use of different dilutions of 4.5 µm activated acridinium microparticles in instrument optics system calibration.

Now referring to FIG. 10, as previously mentioned, the embodiments of the invention are particularly effective for calibrating instruments, such as chemiluminescence-based analytical instruments and the like. In FIG. 10, a bar graph demonstrates the feasibility of using different dilutions of 4.5 μm activated acridinium microparticles for optics calibration of a read system 30.

Figure 11:
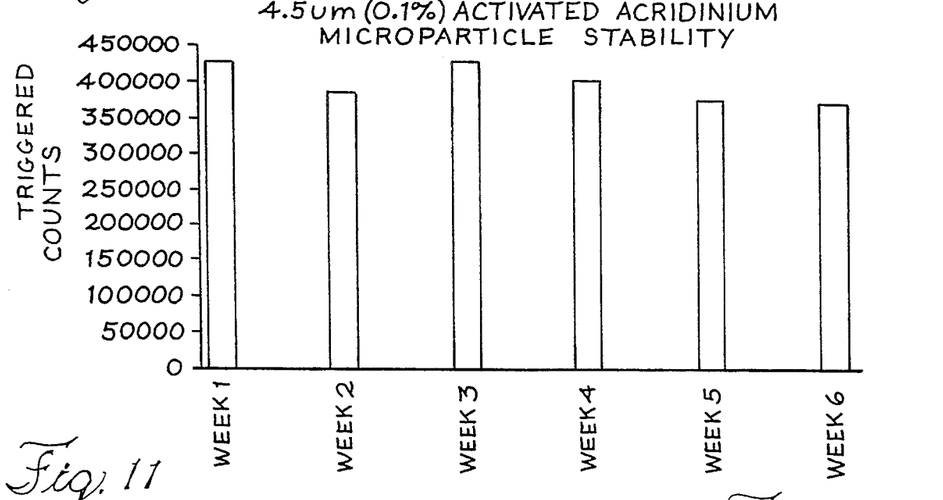
FIG. 11 illustrates the approximately 2–8 degree C. stability of (about 0.1%) 4.5 µm affinity format activated acridinium microparticles.
Figure 12:
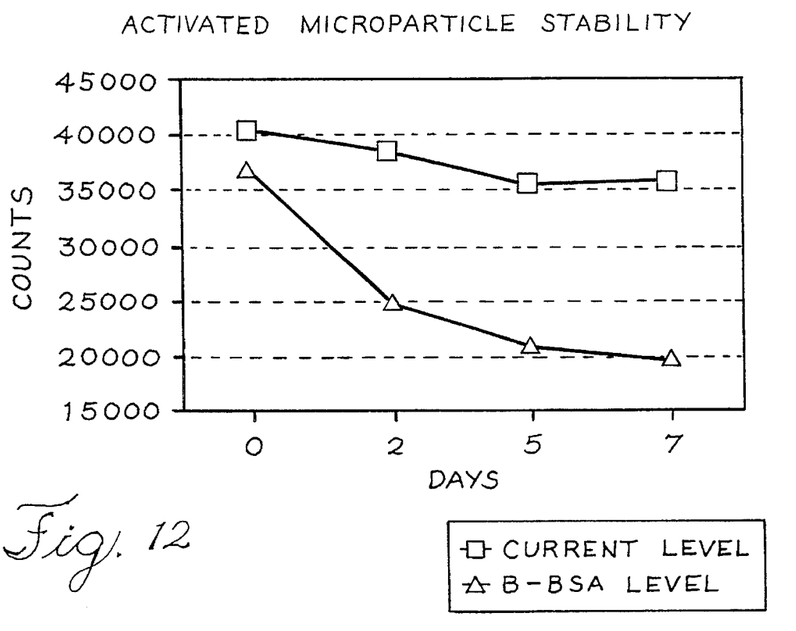
FIG. 12 illustrates the approximately 45 degree C. stability of 5 µm affinity format activated acridinium microparticles compared with the stability of anti-HBsAg coated activated acridinium microparticles.

Referring now to FIGS. 11 and 12, embodiments of the invention provide advantages of environmental and over time stability of activated acridinium microparticles. FIG. 11 shows the approximately 2–8 degrees C. stability over time of (about 0.1%) 4.5 μm affinity format activated acridinium microparticles. FIG. 12 also illustrates the environmental and time stability of activated acridinium microparticles. As shown in FIG. 12, about 45 degrees C. stability over time of 4 μm affinity format activated acridinium microparticles is compared with the prior art anti-HBsAg coated activated acridinium microparticles. As is readily apparent, embodiments of the invention provide significant advantages over the prior technology with respect to stability of activated acridinium microparticles.

Figure 13:
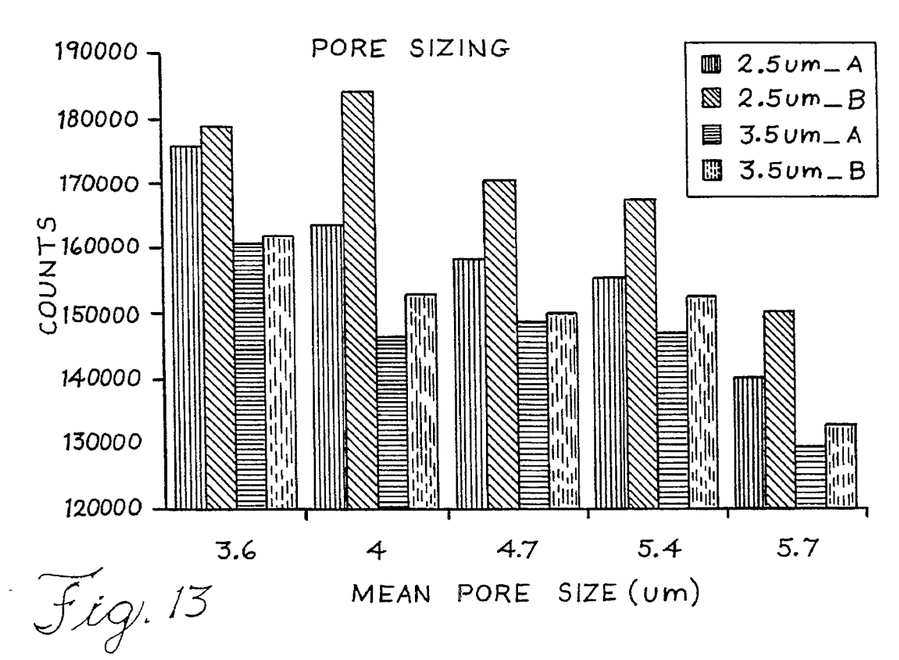
FIG. 13 illustrates the use of different activated acridinium microparticles in determining the pore size on an analytical instrument.

Drawing attention to FIG. 13, utilization of microparticles constructed according to the above-discussed embodiments to determine pore size of an analytical instrument is explored. In an exemplary embodiment, the pore size determined may be physically present on a matrix cell or other read vessel having a capture element, such as a glass fiber matrix and the like. Feasibility of using chemiluminescence of 2.5 μm and 3.5 μm affinity format labelled acridinium activated microparticles for pore sizing is demonstrated. With increasing mean pore size, a decreasing trend in chemiluminescent counts is observed.

Figure 14:
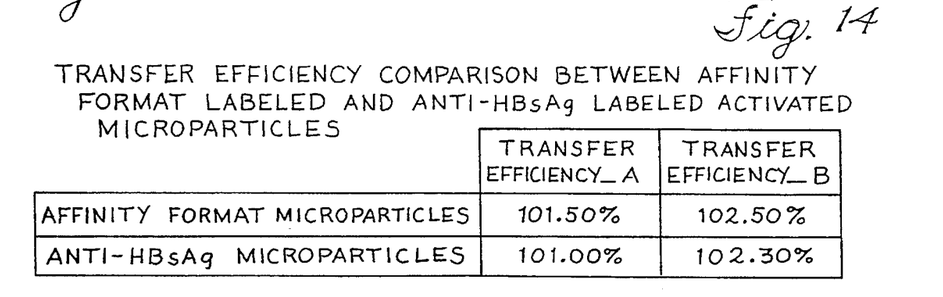
FIG. 14 is a table comparing estimated transfer efficiencies between an affinity format labelled microparticle and an anti-HBsAg labelled microparticle.

In FIG. 14, substantial equivalence between transfer efficiency values or estimates obtained using affinity format microparticles and anti-HBsAg microparticles is demonstrated. Transfer efficiency is the ratio of chemiluminescence counts obtained by triggering about 100 μl of about 0.0033% activated microparticles dispensed directly on a microparticle capture element, such as a glass fiber matrix and the like, to the chemiluminescence counts obtained by dispensing a similar volume of microparticles in a separate area, such as an incubation well on a reaction tray and the like. In an exemplary embodiment, the microparticles are transferred into a reaction well using about 600 μl of transfer solution, and the microparticles are triggered with about 85 μl of an activator solution.

As is clearly seen from the foregoing descriptions and illustrations, the embodiments of the present invention are significant improvements in the art. Those embodiments are believed to be especially effective when performed and employed as described herein, however, those skilled in the art will readily recognize that numerous variations and substitutions may be made in the described embodiments and their use and performance. Each of those variations is intended to be included in the description herein. For instance, while particular solutions and chemical compositions are disclosed, other equivalent solutions and compositions are also possible. The foregoing detailed description is, thus, to be clearly understood as being given by way of illustration and example only, the spirit and scope of the present invention being limited solely by the appended claims.

What is claimed is:

1. A method of preparing an activated acridinium microparticle, the method comprising the steps of:
   (a) activating a 10-methyl-N-tosyl-N-(2-carboxyethyl)-9-acridinium carboximide trifluoromethane sulfonate:
   (b) coating a microparticle with a proteinaceous compound, the proteinaceous compound being selected from the group consisting of albumin and an antibody; and
   (c) coupling activated 10-methyl-N-tosyl-N-(2-carboxyethyl)-9-acridinium carboximide trifluoromethane sulfonate to said proteinaceous compound.

2. The method of claim 1, wherein said proteinaceous compound is bovine serum albumin.

3. The method of claim 1, wherein said activating step (a) comprises the steps of:
   (i) adding a N-hydroxy succinimide solution to said 10-methyl-N-tosyl-N-(2-carboxyethyl)-9-acridinium carboximide trifluoromethane sulfonate; and
   (ii) adding a 1-ethyl-3 carbodiimide solution to said 10-methyl-N-tosyl-N-(2-carboxyethyl)-9-acridinium carboximide trifluoromethane sulfonate.

4. The method of claim 1, wherein said coating step (b) comprises the steps of:
   (i) suspending said microparticle in said proteinaceous compound; and
   (ii) centrifuging said microparticle.

5. The method of claim 1, wherein said coupling step (c) comprises the steps of:
   (i) adding said coated microparticles to a conjugate buffer; and
   (ii) adding said activated 10-methyl-N-tosyl-N-(2-carboxyethyl)-9-acridinium carboximide trifluoromethane sulfonate to said conjugate buffer and said coated microparticle.

6. The method of claim 3, wherein said coating step (b) comprises the steps of:
   (i) suspending said microparticle in said proteinaceous compound; and
   (ii) centrifuging said microparticle.

7. The method of claim 6, wherein said coupling step (c) comprises the steps of:
   (i) adding said coated microparticle to a conjugate buffer; and
   (ii) adding said activated 10-methyl-N-tosyl-N-(2-carboxyethyl)-9-acridinium carboximide trifluoromethane sulfonate to said conjugate buffer and said coated microparticle.

8. Method of preparing an activated acridinium microparticle, the method comprising the steps of:
   (a) activating an anti-biotin labelled 10-methyl-N-tosyl-N-(2-carboxyethyl)-9-acridinium carboximide trifluoromethane sulfonate;
   (b) coating a microparticle with a biotinylated proteinaceous compound, the proteinaceous compound being selected from the group consisting of albumin and an antibody; and
   (c) reacting said microparticle with the activated anti-biotin labelled 10-methyl-N-tosyl-N-(2-carboxyethyl)-9-acridinium carboximide trifluoromethane sulfonate.

9. The method of claim 8, wherein said proteinaceous compound is bovine serum albumin.

10. The method of claim 8, wherein said coating step (b) comprises the steps of:
    (i) suspending said microparticle in said biotinylated proteinaceous compound; and
    (ii) centrifuging said microparticle.

11. The method of claim 8, wherein said reacting step (c) comprises the steps of:
    (i) suspending said microparticle coated with said biotinylated proteinaceous compound in activated anti-biotin labelled with 10-methyl-N-tosyl-N-(2-carboxyethyl)-9-acridinium carboximide trifluoromethane sulfonate.

12. The method of claim 10, wherein said reacting step (c) comprises the steps of:
    (i) suspending said microparticle coated with said biotinylated proteinaceous compound in an activated anti-biotin labelled with 10-methyl-N-tosyl-N-(2-carboxyethyl)-9-acridinium carboximide trifluoromethane sulfonate.

* * * * *